(12) United States Patent
Quapil et al.

(10) Patent No.: US 6,929,943 B1
(45) Date of Patent: Aug. 16, 2005

(54) DEVICE FOR ANALYZING IMMUNOASSAYS

(75) Inventors: Gerald Quapil, Owen/Teck (DE); Manfred Schawaller, Cressier/Au Village (CH)

(73) Assignees: Leuze Electronic GmbH & Co., Owen/Teck (DE); Stiftung fur Diagnostische Forschung, Cressier/sur Morat (CH)

(*) Notice: Subject to any disclaimer, the term of this patent is extended or adjusted under 35 U.S.C. 154(b) by 322 days.

(21) Appl. No.: 09/643,686

(22) Filed: Aug. 24, 2000

(30) Foreign Application Priority Data

Aug. 24, 1999 (EP) ................................ 99116534

(51) Int. Cl.$^7$ ...................... G01N 33/53; G01N 33/543
(52) U.S. Cl. ........................... 435/287.1; 435/4; 435/6; 435/7.1; 435/7.9; 435/7.92; 435/287.3; 435/287.7; 435/287.8; 435/287.9; 435/288.3; 435/288.4; 435/288.5; 435/288.7; 435/808; 436/164; 436/172; 436/518; 436/524; 436/528; 436/805; 436/823; 422/68.1; 422/82.05
(58) Field of Search .......................... 435/4, 6, 7.1, 7.9, 435/7.92, 287.1, 287.3, 287.7–287.9, 288.3–288.5, 435/288.7, 808; 436/164, 172, 518, 524, 436/528, 805, 823; 422/68.1, 82.05

(56) References Cited

U.S. PATENT DOCUMENTS

| | | | |
|---|---|---|---|
| 3,939,350 A | 2/1976 | Kronick et al. | 250/365 |
| 4,451,434 A * | 5/1984 | Hart | 422/102 |
| 5,192,510 A * | 3/1993 | Zoha et al. | 422/82.05 |
| 5,885,530 A * | 3/1999 | Babson et al. | 422/65 |

FOREIGN PATENT DOCUMENTS

| | | |
|---|---|---|
| EP | 0 411 907 A2 | 2/1991 |
| EP | 0 411 907 A3 | 2/1991 |
| WO | 95/22754 | 8/1995 |

OTHER PUBLICATIONS

David S. Hage, "Immunoassays", Anal. Chem. 1999, 71, 294R-304R.

* cited by examiner

Primary Examiner—Chris Chin
Assistant Examiner—Kartic Padmanabhan
(74) Attorney, Agent, or Firm—Venable LLP; Robert Kinberg; Thomas G. Wiseman

(57) ABSTRACT

A device for analyzing immunoassays with a liquid assay medium includes a vessel for holding the assay medium. The vessel has a base comprised of a solid body having a first side wall and a top surface forming a boundary surface of the solid body. First reaction agents are dissolved in the assay medium in the vessel and are labeled with a luminophore or different luminophores and second reaction agents are bonded to the boundary surface within a boundary layer of the assay medium. A transmitter for emitting light rays is arranged so that the light rays are coupled into the base of the vessel via the first side wall and conducted at the total reflection angle to the boundary surface so that luminophore-labeled first reaction agents that are bonded to the second reaction agents are optically excited by at least some of the light rays and emit fluorescent and/or phosphorescent rays. A receiver is positioned for quantitatively detecting the fluorescent rays and/or phosphorescent rays.

20 Claims, 6 Drawing Sheets

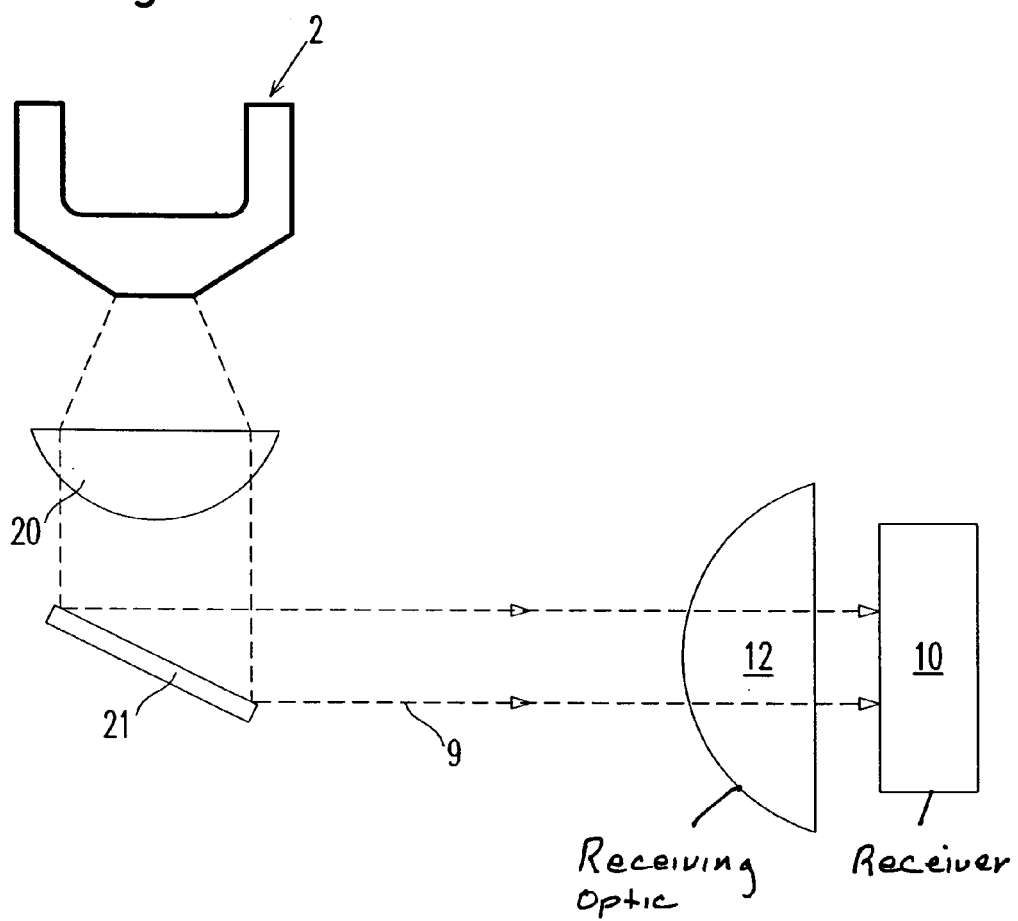

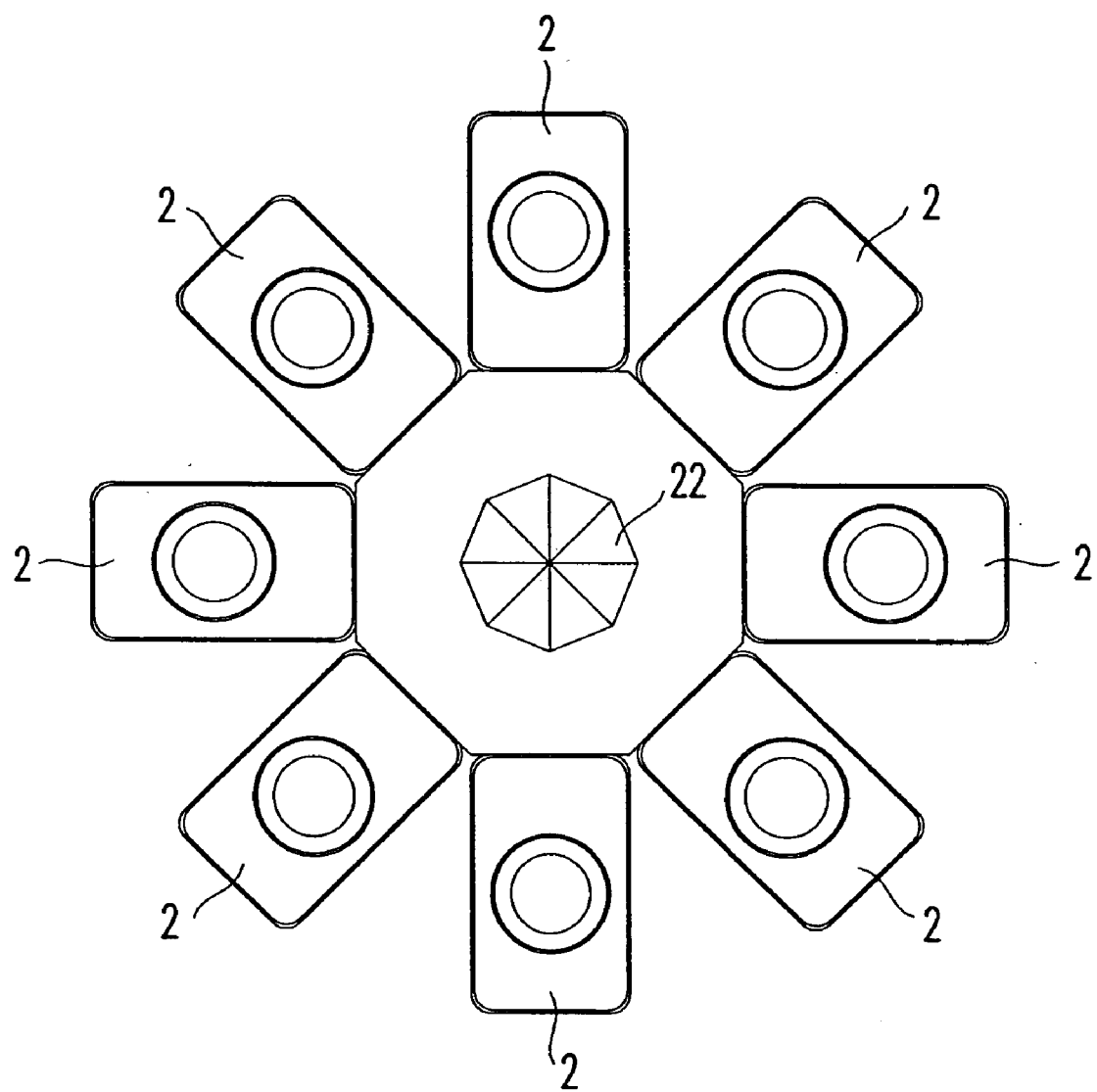

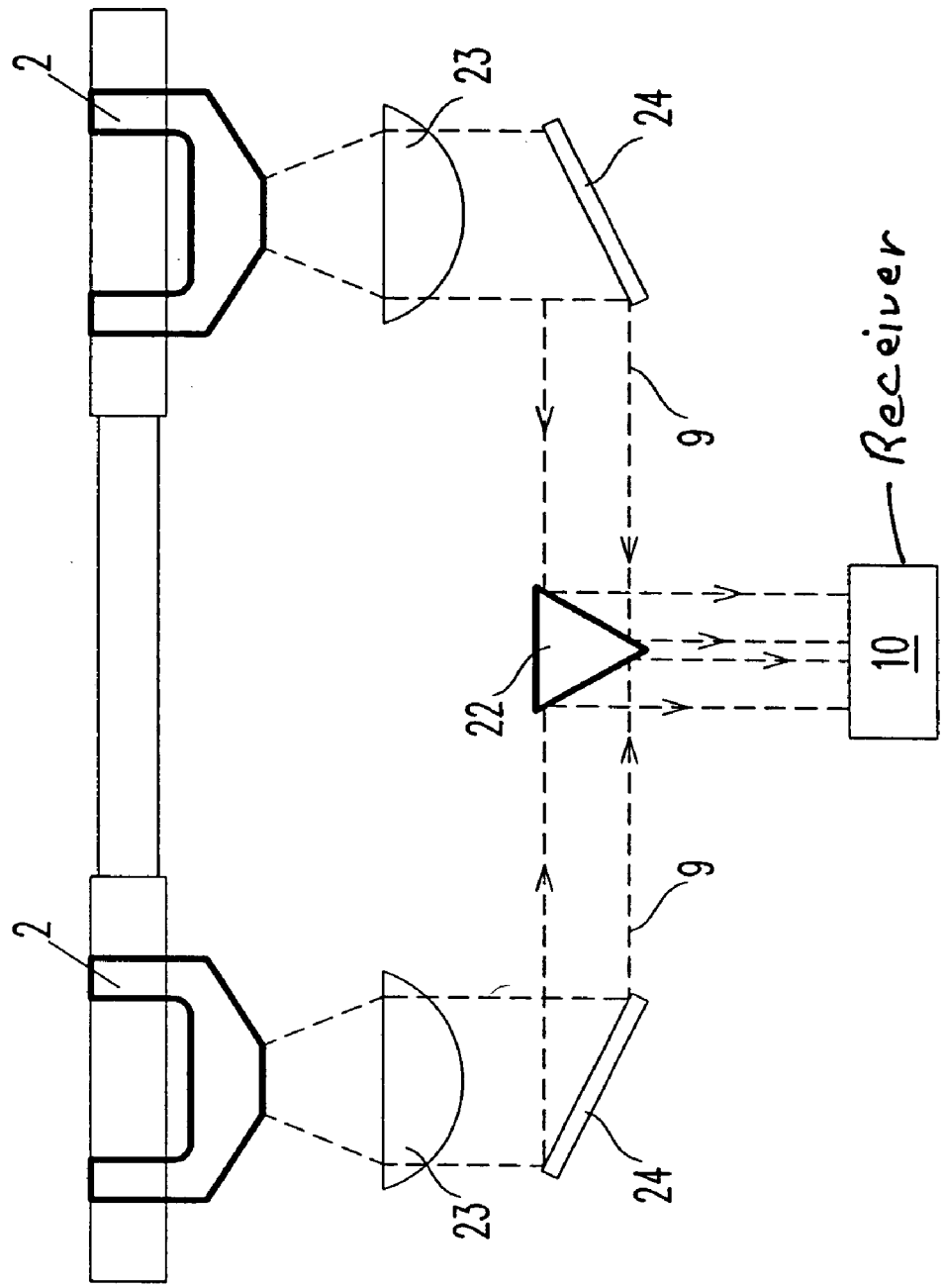

DEVICE FOR ANALYZING IMMUNOASSAYS

CROSS-REFERENCE TO RELATED APPLICATION

This application claims the priority of European Patent Application 99 116 534.1, filed with the European Patent Office on Aug. 24, 1999, the subject matter of which is incorporated herein by reference.

BACKGROUND OF THE INVENTION

The invention relates to a device for analyzing immunoassays with a liquid assay medium which is limited by at least one boundary surface of a solid body, wherein first reaction agents are dissolved in the assay medium and are labeled with a luminophore or different luminophores and second reaction agents are bonded to the boundary surface within a boundary layer of the assay medium, and wherein for a quantitative detection of the first reaction agents with the aid of light rays emitted by a transmitter, an evanescent field is generated through which luminophore-labeled first reaction agents that are bonded to the second reaction agents are optically excited and emit fluorescent rays and/or phosphorescent rays that can be detected in a receiver.

The field of medical diagnostics, specifically immunological diagnostics, is based to a high degree on the ELISA (enzyme-linked immunosorbent assay). A recent overview of immunoassays can be found in Hage, Anal. Chem., Vol. 71, pages 294R–304R, 1999. Two features characterize an ELISA. A first reaction agent is labeled with an enzyme and is dissolved in an assay medium. A second reaction agent is bonded to a solid phase, wherein the solid phase is formed by a boundary surface of a solid body that limits the assay medium.

Standardized plastic panels, frequently made of polystyrene, which contain 96 wells are primarily used for the solid phase. The plastic well surface bonds proteins, which form the second reaction agents, through adsorption in the nanogram range. This amount is sufficient for an immunological detection. A bonding reaction with the first, enzyme-labeled reaction agent present in the solution leads to the bonding of the enzyme to the solid phase. The bonded enzyme is made visible through adding a chromogen substrate that is specific for this enzyme. Subsequently, the resulting colored product can be evaluated optically.

A number of technical options exist for labeling the first reaction agent, mostly an immunoglobulin, with an enzyme. Peroxidase or alkaline phosphatase is commonly used for the labeling.

Excellent results can be obtained with ELISAs with respect to sensitivity and specificity. The achievable detection limits are in the nanogram range or below.

Assays based on this principle are realized in the most varied forms and are used for detecting antigens or antibodies, depending on the problem definition.

However, one significant disadvantage of the ELISA is the handling of the tests because different reagents must be added successively to the wells and must also be removed again. The total of the various pipetting, washing, and incubation steps is different from assay to assay and can number ten or more. For that reason, ELISAs are time-consuming and their performance is very involved operationally. ELISAs must be carried out with great precision by specially trained personnel to achieve good results.

Another disadvantage of the ELISA is the time required for an assay, which is determined by the sum of the incubation and washing steps and normally lasts from one to several hours.

A device for analyzing immunoassays is known from U.S. Pat. No. 3,939,350, for which a transparent disk can be inserted between a prism and a container holding the assay medium.

By means of a laser, transmitted light rays are beamed at the total reflection angle onto the disk, thereby creating an evanescent field in the border region of the assay medium, in the disk area.

The first reaction agent in the solution is labeled with a luminophore. The second reaction agent is bonded to the surface of the disk. If the luminophore-labeled reaction agent in the solution bonds to the surface of the disk, it can subsequently be excited by the evanescent field of a totally reflected light ray and can emit fluorescent radiation. This fluorescent radiation is determined quantitatively and is directly proportional to the bonded luminophore-labeled reaction agent and is thus directly proportional to the amount of the originally existing reaction agent in the solution.

Since only the luminophore bonded to the surface is positioned in the field of evanescence of the laser beam, only this bonded luminophore is optimally excited and emits photons. A luminophore in the solution that is not bonded is not positioned in the field of evanescence of the light beam, is therefore not excited and consequently also does not emit photons. This arrangement therefore permits the quantitative determination of bonded luminophore in the presence of non-bonded luminophore.

However, the disadvantage in this case is the mechanically complicated design of the device. In particular the preparation of the disk and the subsequent insertion of the disk between prism and container are extremely time-consuming. In addition, the preparation can only be carried out by qualified personnel.

SUMMARY OF THE INVENTION

It is an object of the invention to provide a device of the aforementioned type such that an analysis of immunoassays can be carried out with high detection sensitivity and a low expenditure in time, cost and material.

The above and other objects are accomplished according to the invention by the provision of a device for analyzing immunoassays with a liquid assay medium, comprising: a vessel for holding the assay medium and having a base comprised of a solid body, the solid body having a first side wall and a top surface constituting a bottom surface of the vessel and forming a boundary surface of the solid body, wherein first reaction agents are dissolved in the assay medium in the vessel and are labeled with a luminophore or different luminophores and second reaction agents are bonded to the boundary surface within a boundary layer of the assay medium; a transmitter for emitting light rays that are coupled into the base of the vessel via the first side wall and conducted at the total reflection angle to the boundary surface so that luminophore-labeled first reaction agents that are bonded to the second reaction agents are optically excited by at least some of the light rays and emit at least one of fluorescent and phosphorescent rays; and a receiver positioned for quantitatively detecting the at least one of the fluorescent rays and phosphorescent rays.

Thus, according to the invention, the assay medium with the first and second reaction agents as well as the luminophore is located inside a vessel, wherein the second reaction agent is bonded to the top surface that forms the boundary surface of the base of the vessel.

The light rays emitted by the transmitter are coupled in and refracted via a wall on the side of the base, so that these rays travel in the base and are conducted onto the boundary surface at the angle of total reflection. The fluorescent rays and/or the phosphorescent rays emitted by the luminophores are recorded inside the receiver.

The light-deflecting and light-conducting means for producing the field of evanescence thus can be produced simply and cheaply through a suitable design of the vessel base. It is particularly advantageous in this case that the light-deflecting and light-conducting means, as well as the receptacle for the assay medium, are formed by a vessel that is preferably designed as one piece.

Preferably, the upper edge of the vessel has an additional attachment for fastening the vessel to a holder.

The analysis of immunoassays thus can be carried out with a low number of operational steps. In particular, hardly any effort is required for preparing the assays.

It is also advantageous that the device according to the invention comprises few individual parts, requires little assembly effort and also has small dimensions as well as a low weight, so that it is easy to handle and in particular can also be designed to be mobile.

An especially advantageous embodiment can also provide for an arrangement of multiple vessels, wherein these vessels are stationary arranged and can be examined with the aid of a multiple arrangement of transmitters. In this case, a common receiver records the fluorescent rays and/or the phosphorescent rays coming from the individual vessels.

This arrangement is simple and can be produced cheaply. Furthermore, it is advantageous that no moving parts are required for this arrangement, thereby keeping the calibration expenditure low.

BRIEF DESCRIPTION OF THE DRAWINGS

These and other features and advantages of the invention will be further understood from the following detailed description of the preferred embodiments with reference to the accompanying drawings.

FIG. 6 is a cross section through a portion of the device according to FIG. 5.

FIG. 7 is a schematic illustration of a third embodiment for analyzing immunoassays with a second multiple arrangement of vessels.

FIG. 8 is a cross section through the device according to FIG. 7.

DETAILED DESCRIPTION OF THE PREFERRED EMBODIMENTS

Figure 1:
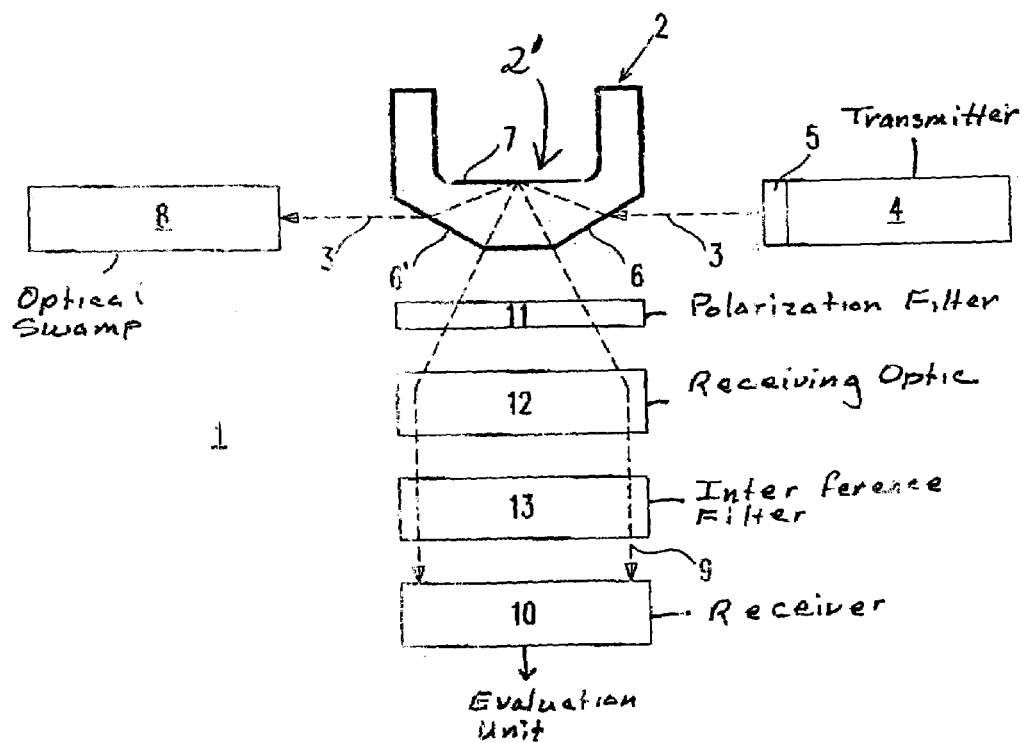
FIG. 1 is a schematic representation of a first exemplary embodiment of a device for analyzing immuno-assays, comprising a vessel for holding an assay medium.

FIG. 1 shows a first embodiment of a device 1 for analyzing immunoassays according to the invention. The immunoassay to be analyzed is located in a vessel 2. An optical sensor arrangement is provided for analyzing the assay. The sensor arrangement comprises a transmitter 4 in the form of a laser, which emits light rays 3. A polarization filter 5 is installed downstream of transmitter 4 for a linear polarization of light rays 3, which are focused onto vessel 2.

Transmitter 4 is arranged in front of a slanted sidewall 6 of a base 2' of vessel 2. The slant for side wall 6 is selected such that the arriving light rays 3 are refracted at side wall 6 toward a top surface 7 of base 2' and arrive there at the angle of total reflection. The inclination of sidewall 6 furthermore is selected such that light rays 3 arrive at the Brewster angle. As a result of this, the polarization of the light rays 3 remains the same when entering vessel 2. In addition, there are no intensity losses. The top surface 7 of base 2' constitutes a boundary surface for the immunoassay. For convenience surface 7 is alternately referred to herein as the top surface of base 2' or the boundary surface for the immunoassay. Consequently, nearly the total amount of light from transmitted light rays 3 is reflected at top surface 7 of the base and conducted to a second side wall 6 of base 2' of vessel 2. Light rays 3 are refracted again at second side wall 6' and strike an optical swamp 8, which prevents light rays 3 from being reflected back onto vessel 2. The beam guidance of light rays 3 is selected such that on the outside of vessel 2, the light rays extend in horizontal direction and parallel to the top surface of the base for vessel 2.

Despite the fact that light rays 3 approach the boundary surface at the total reflection angle, a small portion of transmitted light rays 3 penetrates to the inside of vessel 2 and forms an evanescent field inside a boundary layer. This portion decreases exponentially with the distance to boundary surface 7. In this case, the penetration depth of the evanescent field is deeper than the surface roughness of the surface for vessel 2.

Among other things, vessel 2 contains luminophores. The luminophores in the exemplary embodiments shown are optically excited in the boundary layer and emit fluorescent rays 9. The portion of fluorescent rays 9 that penetrates the base of vessel 2 strikes a receiver 10, which is arranged at a distance underneath vessel 2. Receiver 10 is formed either by a PIN detector, a photo-multiplier or an avalanche diode.

In order to improve the detection sensitivity, a polarization filter 11, a receiving optic 12 in the form of a collective lens, as well as an interference filter 13 are installed in front of receiver 10.

Receiver 10 and transmitter 4 are connected to an evaluation unit (not shown here) which may comprise, for example, a microcontroller or the like. The receiving signals present at the output of receiver 10 are evaluated in the evaluation unit. In addition, the evaluation unit controls transmitter 4.

Vessel 2 contains an assay medium, which is typically a watery solution. The assay medium contains a first reaction agent that is detected quantitatively by device 1 according to the invention. First reaction agents typically are antigens or antibodies. A second reaction agent, for example a protein, is bonded by means of adsorption to boundary surface 7 of vessel 2.

The first reaction agent in solution is labeled with the luminophore. The second reaction agent is bonded to the boundary surface 7 of vessel 2. If the luminophore-labeled first reaction agent from the solution bonds to the second reaction agent at the boundary surface, it can then be excited by the evanescent field of the totally reflected transmitted light rays 3 and can emit fluorescent rays 9. These fluorescent rays 9 are quantitatively detected in receiver 10 and are directly proportional to the bonded, luminophore-labeled reaction agent and thus directly proportional to the amount of the originally existing first reaction agent in the solution.

Since only the luminophore bonded to the surface is positioned in the evanescent field of the transmitted light rays 3, only this luminophore is excited and emits fluorescent rays 9. Non-bonded luminophore in the solution is not positioned in the evanescent field, is therefore not excited and thus does not emit any fluorescent rays 9. This arrangement consequently permits the quantitative determination of bonded luminophore in the presence of non-bonded luminophore, without requiring a prior separation and washing step.

After adding the first reaction agent to vessel 2, it makes sense in this case to directly measure the increase in the bonded luminophore over time as the reaction progresses. Since the amount of bonded luminophore is directly proportional to the originally existing amount of luminophore, the sensor arrangement makes it possible to make a quantitative determination of reactant in the solution, in real time and without additional washing and/or pipetting steps, except for the initial pipetting step.

Since the absorption coefficients and the emission properties for luminophores are very favorable, there are low detection limits. Reactions can be measured and quantified after several minutes already.

When evaluating the receiving signals present at the receiver 10, the dark noise of receiver 10, and the photo counting unit integrated therein, is initially emitted prior to analyzing the immunoassay. In the process, the square root $\sqrt{N}$ of the recorded rate N for the photons is determined as the standard deviation for the dark noise.

For a quantitative detection of the first reaction agent in vessel 2, the receiving signal that increases during the analysis of the immunoassay must reach a multiple of the standard deviation during a specified measuring interval. At the same time, the shape of the increase of the receiving signal must satisfy the shape of an exponential function with a time constant within predetermined tolerance limits. The mathematically adapted values for the time constant, the amplitude and the offset of the receiving signal must be within predetermined limits. Finally, the sum of the deviations from measured values and the mathematical curve, adapted to these, must not exceed a specified value.

The aforementioned parameters can vary corresponding to the changing content in vessel 2.

Figure 2:
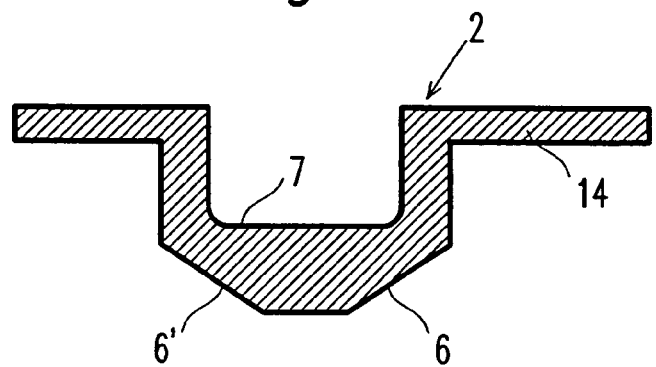
FIG. 2 is a cross section through the vessel according to FIG. 1.
Figure 3:
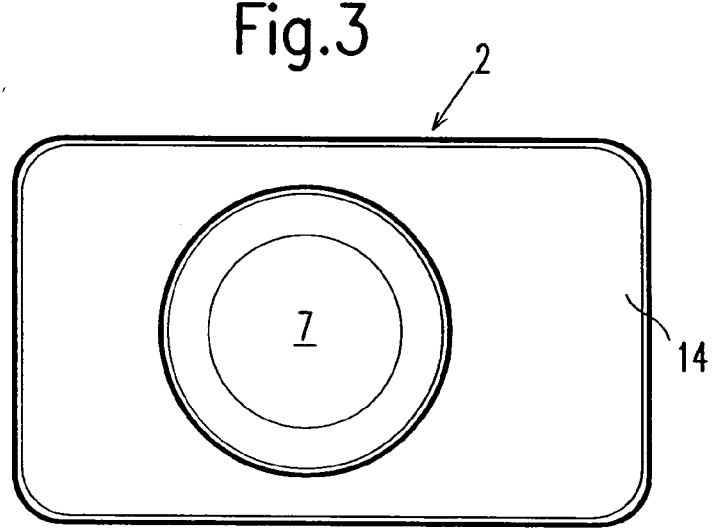
FIG. 3 is a view from above of the vessel according to FIG. 1.

The design for vessel 2 follows from FIG. 1 and, in particular, from FIGS. 2 and 3. Vessel 2 essentially comprises a hollow-cylindrical base body and is open toward the top.

The base 2' of vessel 2 consists of a massive circularly cylindrical base body, wherein the envelope surface is slanted on opposite sides. The resulting sidewalls 6, 6' approach the flat underside 6" of the base at a slanted angle. The flat sidewalls 6, 6 are arranged in mirror symmetry to base 2' body of vessel 2. The inclination angles of the surfaces of sidewalls 6, 6' for vessel 2 are adapted so that, after accounting for the refraction indices of the vessel material and the assay medium contained inside vessel 2, light rays 3 will be refracted at side wall 6 of vessel 2 so as to strike boundary layer 7 at the total reflection angle as shown in FIG. 1. After being reflected, light rays 3 are then correspondingly coupled out via second sidewall 6' of vessel 2.

Referring to FIGS. 2 and 3, vessel 2 has an attachment 14, which adjoins the upper edge of the hollow cylindrical base body. Attachment 14 is shaped like a disk and has essentially the shape of a plate with rectangular cross section. Vessel 2 is secured relative to the sensor arrangement by securing it with attachment 14 to a holder that is not shown here. Vessel 2 preferably is secured with opposite-arranged side edges of attachment 14. The side edges or the top surface of attachment 14 can also have markings for identifying the content of vessel 2. In particular, these markings can be in the form of bar codes.

Vessel 2, comprising a base body and attachment 14, is preferably formed as one piece and more preferably consists of an extrusion-molded plastic part. Vessel 2 in this case preferably is made of polystyrene.

The open top of vessel 2 can be closed off with a foil or the like. Following that, the immunoassay to be analyzed can be injected through the foil into vessel 2, for example with an injection needle.

With the arrangement according to FIG. 1, light rays 3 that are emitted by transmitter 4 are coupled into the vessel 2 and, following a one-time total reflection at the boundary surface 7 of vessel 2, are again coupled out of the vessel and finally transmitted to optical swamp 8. The disadvantage here is that only a small portion of the luminophores present in the boundary layer is optically excited, owing to the small diameter of the transmitted light rays 3, which typically is much smaller than the size of boundary layer 7.

Figure 4:
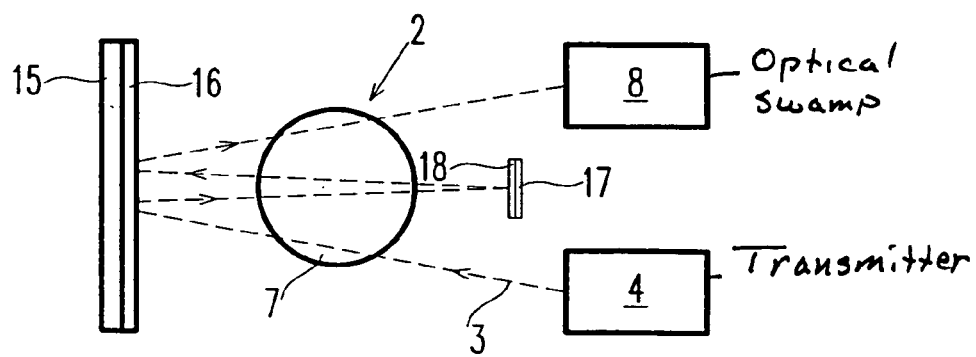
FIG. 4 is a partial section of a second embodiment for analyzing immunoassays.

The arrangement according to FIG. 4 can be provided to remedy this disadvantage. Following the first passage through vessel 2, this arrangement permits light rays 3 to be reflected on a first mirror 15 with upstream installed polarization filter 16 and to be coupled into vessel 2 once more by second side wall 6' of base 2', such that transmitted light rays 3 are again reflected with the total reflection angle on boundary surface 7. Transmitted light rays 3, which exit from vessel 2 following the reflection, subsequently strike a second mirror 17 with upstream-installed polarization filter 18 and are again coupled into vessel 2. Following a total reflection at boundary surface 7, light rays 3 again strike the mirror 15. From there, light rays 3 are once more coupled into vessel 2 and, following total reflection at boundary surface 7, strike optical swamp 8. Transmitter 4, mirrors 15, 17, as well as optical swamp 8, are essentially arranged in one plane that extends through the vessel base and are displaced to the side, relative to each other, so that during the individual passages through vessel 2, light rays 3 arrive at respectively different locations of boundary surface 7. As a result, a considerable portion of the boundary surface 7 is optically excited by means of transmitted light rays 3.

Figure 5:
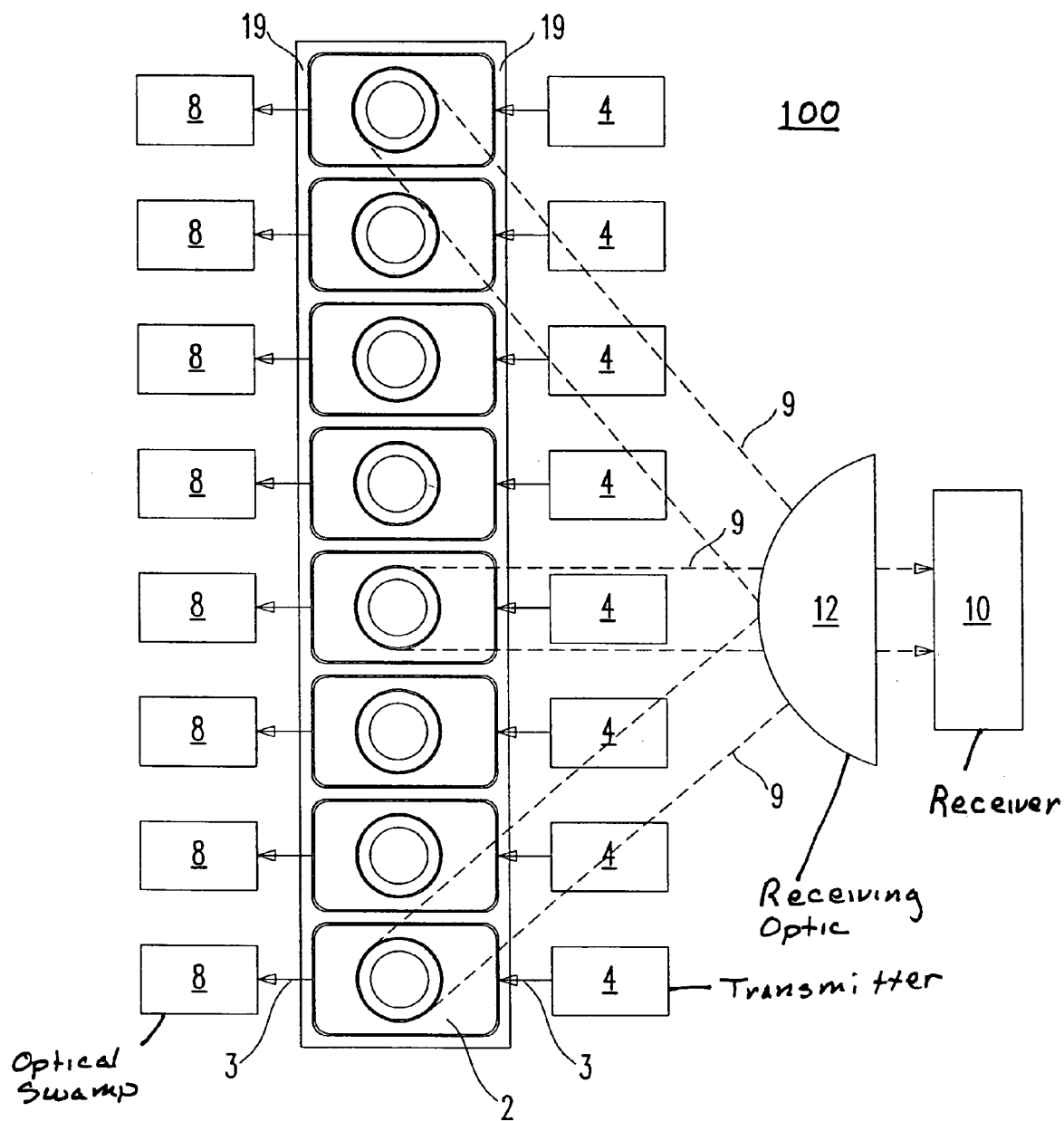
FIG. 5 is a schematic illustration of a third embodiment for analyzing immunoassays with a first multiple arrangement of vessels.

FIGS. 5 and 6 show a device 100 with an arrangement of multiple vessels 2. Vessels 2 in this case are arranged in a line, one after another, and are positioned inside a frame 19, which serves as a holder. A transmitter 4 and an optical swamp 8 are respectively assigned to each vessel 2.

Fluorescent rays 9, exiting on the underside of the bases for the vessels 2, are conducted via receiving optic 12 to receiver 10. An interference filter and a polarization filter are installed in front of receiver 10, in the same way as in FIG. 1. These are not shown in FIGS. 5 and 6 for reasons of clarity.

A lens 20 and a subsequently installed reflecting mirror 21 are arranged below each vessel 2. Transmitted light rays 3 that exit from vessel 2 are collected by means of lens 20 and are focused onto reflecting mirror 21. The respective reflecting mirrors 21, which are assigned to individual vessels 2, are oriented such that the thereon-reflected fluorescent rays 9 arrive at receiver 10 by way of receiving optic 12. For reasons of clarity, only fluorescent rays 9 that emanate from three vessels 2 are shown in FIG. 5. The fluorescent rays 9 emanating from the remaining vessels 2 are not drawn in.

With the aid of an evaluation unit (not shown), transmitters 4 are individually activated one after another, so that fluorescent rays 9 exiting from separate vessels 2 can be evaluated separately.

FIGS. 7 and 8 show another embodiment according to the invention with a different arrangement of multiple vessels 2. FIG. 7 shows a concentric arrangement of vessels 2, wherein a stationary polygonal mirror 22 is arranged in the center of the arrangement. Each vessel 2 in turn is coordinated with a transmitter 4 and an optical swamp 8, which are not shown in FIGS. 7 and 8. Vessels 2 are positioned in a non-depicted holder. Transmitters 4 and optical swamps 8 are also arranged stationary in the specified positions relative to the respective vessel 2.

As can be seen especially in FIG. 8, vessels 2 are positioned in one plane, while polygonal mirror 22 is located underneath vessels 2. A lens 23 and a reflecting mirror 24 are assigned to each vessel 2 and are arranged below the base of the respective vessel 2. Fluorescent rays 9 that exit from the bottom of each base for the respective vessel 2 are collected with lens 23 and focused onto reflecting mirror 24. The thereon-reflected fluorescent rays 9 are then deflected toward polygonal mirror 22 and are conducted to receiver 10, arranged underneath polygonal mirror 22. A receiving optic, which is installed in front of receiver 10, as well as a polarization filter and an interference filter, although not shown in FIG. 8, are employed in a manner similar to that shown and discussed in connection with FIG. 1.

Transmitters 4 in turn are activated individually, one after another, so that fluorescent rays 9 that exit from individual vessels 2 can be evaluated separately.

The illustrated exemplary embodiments of the device according to the invention can also be expanded to use luminophores that emit fluorescent rays 9 and/or phosphorescent rays. In particular, organic and organometallic coloring agents are used in this case.

Since the phosphorescent radiation has a longer emission interval the fluorescent radiation, the phosphorescent radiation is emitted with a delay relative to the fluorescent radiation, wherein the delay times are in the µs to ms range.

In the simplest case, vessel 2 contains only one type of first reaction agents, which are labeled with a luminophore. Depending on the luminophore composition, these emit phosphorescent rays and/or fluorescent rays 9, which are then evaluated in receiver 10.

Desirably, the detection of the phosphorescent rays occurs by means of a photon count in receiver 10, while transmitter 4 is turned off.

In one advantageous embodiment, vessel 2 of the invention contains two different types of first reaction agents, which are labeled with different luminophores. The first luminophores have a high fluorescence and low phosphorescence, so that they essentially emit only fluorescent rays 9 when optically excited. The second types of luminophores have high phosphorescence and a low fluorescence, so that they essentially emit only phosphorescent rays when optically excited.

In order to be able to detect the phosphorescent radiation separately from the fluorescent rays 9, transmitter 4 is operated in the pulsed mode. The pulse-break ratio of the light pulses, emitted by transmitter 4, is selected such that fluorescent rays 9 are emitted during the emission of light pulses and phosphorescent rays are emitted during the transmitting breaks.

In this way, both types of first reaction agents can be detected quantitatively through a separate analysis of the fluorescent rays of the first luminophores, tied to the first type of reaction agent, and the phosphorescent rays of the second luminophores, tied to the second type of the first reaction agent.

It will be understood that the above description of the present invention is susceptible to various modifications, changes and adaptations, and the same are intended to be comprehended within the meaning and range of equivalents of the appended claims.

What is claimed is:

1. A device for analyzing sandwich immunoassays with a liquid assay medium, comprising:
   a plurality of vessels for holding the assay medium, each of the vessels having a base comprised of a solid body, the solid body having a first side wall and a top surface constituting a bottom surface of the vessel and forming a boundary surface of the solid body, wherein first reaction agents are dissolved in the assay medium in the vessel and are labeled with a luminophore or different luminophores and second reaction agents are bonded to the boundary surface within a boundary layer of the assay medium;
   a plurality of transmitters for emitting light rays that are coupled into the base of each vessel via the first side wall and conducted at a total reflection angle to the boundary surface so that luminophore-labeled first reaction agents that are bonded to the second reaction agents are optically excited by at least some of the light rays and emit at least one of fluorescent and phosphorescent rays;
   a polygonal mirror; and
   a receiver positioned for quantitatively detecting the at least one of the fluorescent rays and phosphorescent rays,
   wherein the plurality of transmitters are activated individually, one after another, and the plurality of vessels are arranged concentrically to the polygonal mirror so that the fluorescent rays exiting at the vessels are conducted via the polygonal mirror to the receiver, and the receiver is a common receiver for recording the fluorescent rays exiting from the individual vessels.

2. The device according to claim 1, wherein the base of the vessel has a second side wall arranged opposite from the first side wall, wherein both the first and second side walls are flat and extend at an angle of less than 90° to the boundary surface, the transmitted light rays are coupled into the base via the first side wall and, following a total reflection at the boundary surface, are coupled out via the second side wall.

3. The device according to claim 2, wherein the first and second side walls of the base extend symmetrically to a symmetry plane of the base.

4. The device according to claim 2, wherein the vessel has an essentially hollow-cylindrical shape, the base is circularly cylindrical, and the first and second sidewalls comprise sloping sides for the circularly cylindrical base.

5. The device according to claim 1, wherein each of the vessels has an open top presenting an upper edge, and the device further includes a disk-shaped attachment adjoining the upper edge for facilitating insertion of the vessel into a holder.

6. The device according to claim 5, wherein the attachment has a rectangular cross section presenting longitudinal sides that can be attached to the holder.

7. The device according to claim 5, wherein the attachment has one side edge for receiving a marking characterizing the content of the vessel.

8. The device according to claim 5, wherein the vessels and attachment comprise one piece.

9. The device according to claim 1, wherein each of the vessels comprises an injection-molded plastic part.

10. The device according to claim 9, wherein the vessels are comprised of polystyrene.

11. The device according to claim 1, wherein the transmitters are arranged so that the transmitted light rays outside of the vessel extend parallel to the boundary surface of the vessel.

12. The device according to claim 1, wherein the base has an underside and the receiver is arranged so that the at least one of the fluorescent rays and phosphorescent rays are coupled out via the underside of the base and conducted to the receiver.

13. The device according to claim 1, further comprising an optical swamp arranged so that the light rays transmitted into the base via the first side wall are conducted to the optical swamp after the light rays exit from the vessel.

14. The device according to claim 1, wherein each of the transmitters comprises a laser and a polarization filter connected downstream of the laser.

15. The device according to claim 13, further comprising an arrangement of mirrors and upstream connected polarization filters for transmitting the light rays repeatedly through the bases of the vessels and onto the boundary surface.

16. The device according to claim 1, wherein the transmitters are operable in a pulsed mode having a pulse-break ratio of transmitting light pulses selected such that optically excited luminophores emit fluorescent rays during emission of a transmitting light pulse and emit phosphorescent rays during transmitting breaks.

17. The device according to claim 16, wherein the different luminophores include first and second luminophores, the first luminophores having a high fluorescence and low phosphorescence and the second luminophores having high phosphorescence and a low fluorescence.

18. The device according to claim 16, wherein the receiver detects the first reaction agents with a time delay such that the fluorescent rays from the first luminophores are recorded during the emission of the transmitting light pulses and the phosphorescent rays from the second luminophores are recorded during the transmitting breaks.

19. The device according to claim 1, wherein the receiver is one of a photo-multiplier, a PIN detector, and an avalanche diode, and includes a polarization filter, a receiving optic, and an interference filter installed in front of the receiver.

20. A device for analyzing immunoassays with a liquid assay medium, comprising:

a plurality of vessels, each vessel having a well with a lower portion for holding the assay medium and having a base which has a top layer that defines the lower portion of the well and a first side wall, which is capable of receiving light rays and reflecting them to the top layer where a second reaction component is bound;

a plurality of transmitters, each transmitter for emitting light rays to the base of each vessel via the first side wall and conducted at a total reflection angle to a boundary surface formed between the bound second reaction component and the assay medium so that luminophore-labeled first reaction agents that are bonded to the second reaction agents are optically excited by at least some of the light rays and emit at least one of fluorescent and phosphorescent rays;

a receiver positioned underneath the base to receive at least one of the emitted fluorescent rays and phosphorescent rays and thereby permit a direct quantitative measurement of an analyte of interest;

a polygonal mirror; and a plurality of optical swamps positioned to receive the reflected light rays, wherein the assay medium contains first reaction agents which are labeled with a luminophore or different luminophores and sample suspected of containing an analyte of interest wherein the plurality of transmitters are activated individually, one after another, and the plurality of vessels are arranged concentrically to the polygonal mirror so that the fluorescent rays exiting at the vessels are conducted via the polygonal mirror to the receiver, and the receiver is a common receiver for recording the fluorescent rays exiting from the individual vessels and the plurality of optical swamps are arranged so that the light rays transmitted into the base via the first side wall are conducted to the optical swamp after the light rays exit from the vessel.

* * * * *